US00PP17266P2

(12) United States Plant Patent
Sanders

(10) Patent No.: US PP17,266 P2
(45) Date of Patent: Dec. 12, 2006

(54) ***IMPATIENS* PLANT NAMED 'IMTRALILA'**

(50) Latin Name: *Impatiens walleriana*
Varietal Denomination: Imtralila

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 91 days.

(21) Appl. No.: 11/203,690

(22) Filed: Aug. 15, 2005

(51) Int. Cl.
*A01H 5/00* (2006.01)

(52) U.S. Cl. ..... Plt./317
(58) Field of Classification Search ..... Plt./317
See application file for complete search history.

*Primary Examiner*—Kent Bell
(74) *Attorney, Agent, or Firm*—Bruce Vrana

(57) ABSTRACT

A new *Impatiens* plant, characterized particularly as to novelty by a flat and strong outward spreading growth habit, freely branching with branches that tend to grow horizontally, resulting in a big and very floriferous plant with large lilac flowers.

1 Drawing Sheet

Latin name of the genus and species of the plant claimed: *Impatiens walleriana.*
Varietal denomination: 'Imtralila'.

BACKGROUND OF THE NEW PLANT

The present invention comprises a new distinct cultivar of *Impatiens,* botanically known as *Impatiens walleriana.*

The new *Impatiens* is a product of a planned breeding program conducted in Enkhuizen, Netherlands. The new *Impatiens* cultivar is characterized by a flat and spreading growing habit, freely branching with branches that tend to grow horizontally resulting in a floriferous plant with large, lilac flowers.

The present cultivar originated from a cross-pollination made in 2001, of a proprietary *Impatiens walleriana* selection identified as 'R3617-1,' not patented, as the female, or seed parent, with a proprietary *Impatiens walleriana* selection identified as 'R2167-2,' not patented, as the male, or pollen parent. 'Imtralila' differs from its parents primarily in flower color.

The present cultivar has been repeatedly asexually reproduced by cuttings in Enkhuizen, Netherlands, in Angers, France and in Gilroy, Calif. over a three-year period. The distinctive characteristics of this new *Impatiens* are stable and reproduced true to type in successive generations of asexual reproduction. It takes 6 to 8 weeks to produce a finished plant, depending on the temperature.

This new *Impatiens* plant is an annual in most climatical zones in the USA, only in zones 9 and 10 it is a perennial plant.

DESCRIPTION OF THE DRAWING

This new *Impatiens* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new *Impatiens.* The data which defines these characteristics were collected from asexual reproductions carried out in Enkhuizen, Netherlands. The plant history was taken on 25 week old plants, blossomed under natural light in the field.

Color readings were taken in the office under ambient light. Color references are primarily to The R.H.S. Color Chart of The Royal Horticultural Society of London.

TABLE 1

Differences between the new cultivar 'Imtralila' and a similar cultivar

| | 'Imtralila' | 'Imtrarose' |
|---|---|---|
| Flower color | Lilac | Rose |
| Habit | Slightly upright and spreading | Long trailing branches |

'Imtrarose', co-pending U.S. Plant patent application Ser. No. 11/051,269.

The plant:
Parentage:
*Female parent.*—'R3617-1,' not patented.
*Male parent.*—'R2167-2,' not patented.
Propagation:
*Type cutting.*—Terminal cuttings.
*Time to initiate roots.*—10–12 days at 20° C.
*Time to produce a rooted cutting.*—4 weeks.
*Root description.*—Fine, fibrous, and white in color.
Plant description:
*General appearance.*—Makes long branches that tend to grow horizontally.
Habit:
*Growth and branching habit.*—Freely branching habit, freely flowering, vigorous.
*Plant height.*—22–26 cm.
*Plant spread.*—90–106 cm.
Lateral branch description:
*Length.*—30–52 cm.
*Diameter.*—3.5–6 mm.
*Texture.*—Smooth, glabrous.
*Internode length.*—0.6–8 cm.
*Color.*—RHS 145B to 145D and 183B.

Foliage description:
*Arrangement.*—Alternate.
*Length, mature leaves.*—5.8–7.2 cm.
*Width, mature leaves.*—3–3.5 cm.
*Shape.*—Broadly elliptic.
*Apex.*—Acuminate.
*Base.*—Acute.
*Margin.*—Serrate.
*Texture.*—Smooth, glabrous.
*Venation pattern.*—Pinnate.
*Color young foliage, upper surface.*—RHS 146A.
*Color young foliage, lower surface.*—RHS 147C and 182B.
*Fully expanded foliage, upper surface.*—RHS 146A.
*Fully expanded foliage, lower surface.*—RHS 147C and 182B.
*Venation, upper surface.*—RHS 144A.
*Venation, lower surface.*—RHS 146B.
*Petiole length.*—About 1.9–3 cm.
*Petiole diameter.*—About 2.5 mm.
*Texture.*—Smooth, glabrous.
*Color.*—RHS 145C and a bit 181A.

Flower description:
*Flower type and flowering habit.*—Single.
*Number of flowers per leaf axil.*—3–4.
*Number of flowers and flower buds per lateral branch.*—23–33.
*Flower position.*—Above and beyond the foliage and typically facing upwards and outward.
*Flower shape.*—Rounded, mostly flat.
*Flowers lasting.*—About 7–9 days on the plant depending on environmental conditions.
*Flowers.*—Non persistent and not fragrant.
*Flowering.*—Indeterminate and continuous.
*Flowering season.*—Year round under greenhouse conditions. In the garden, flowering from spring until fall.
*Flower diameter.*—About 4.5 cm.

Flower buds:
*Rate of opening.*—From flower bud to fully open flower, typically about 6–8 days, depending on temperature.
*Bud length* (*at stage of showing color*).—About 1.4 cm.
*Bud diameter.*—About 0.9 cm.
*Bud shape.*—Ovoid.
*Texture.*—Smooth, glabrous.
*Color, just before opening.*—RHS N74B.

Petals:
*Quantity.*—Single, five per flower, imbricate.
*Length of banner petal.*—About 1.7–2.1 cm.
*Width of banner petal.*—About 2.5–3 cm.
*Length lateral and basal petals.*—About 2.4–2.7 cm.
*Width lateral and basal petals.*—About 1.9–2.1 cm.
*Lateral and basal petal shape.*—Obovate.
*Banner petal shape.*—Broadly obcordate.
*Petal apex.*—Retuse to emarginate.
*Petal base.*—Attenuate.
*Petal margin.*—Entire.
*Petal texture.*—Smooth, satiny.
*Petal color.*—Upper surface: When opening and fully opened: RHS N74A. Small middle eye: RHS 61A. Lower surface: When opening and fully opened: RHS N78B.

Sepals:
*Lateral sepals.*—2.
*Shape.*—Ovate-lanceolate.
*Apex.*—Acute.
*Margin.*—Entire.
*Length.*—3–7 mm.
*Texture upper and lower surface.*—Smooth, glabrous.

Spur:
*Length.*—About 2.5 cm.
*Texture.*—Smooth, glabrous.
*Aspect.*—Curved.
*Color.*—RHS 184A.

Peduncles:
*Length.*—About 1.5–2.6 cm.
*Diameter.*—1 cm.
*Aspect.*—About 45° from the stem.
*Color.*—RHS 145A.
*Bracts.*—At least 2.
*Shape.*—Subulate.
*Apex.*—Acute.
*Length.*—3–6 mm.
*Color.*—RHS 144A.

Reproductive organs:
*Androecium.*—Stamen number: Five fused at anthers, filaments free, hooded.
*Anther shape.*—Oval.
*Anther length.*—About 5 mm.
*Anther color.*—RHS 71A.
*Amount of pollen.*—No pollen.

Gynoecium:
*Pistil number.*—One.
*Pistil length.*—About 4.5 mm.
*Stigma shape.*—Columnar, five segmented.
*Stigma color.*—Red purple.
*Style color.*—RHS 72A.
*Ovary arrangement.*—Five celled.
*Ovary color.*—RHS 146A.
*Seed development.*—Seed development has not been observed.
*Disease/pest tolerance.*—No known susceptibility to diseases or insects noted to date.

What is claimed is:

1. A new and distinct cultivar of *Impatiens* plant named 'Imtralila', as substantially illustrated and described herein.

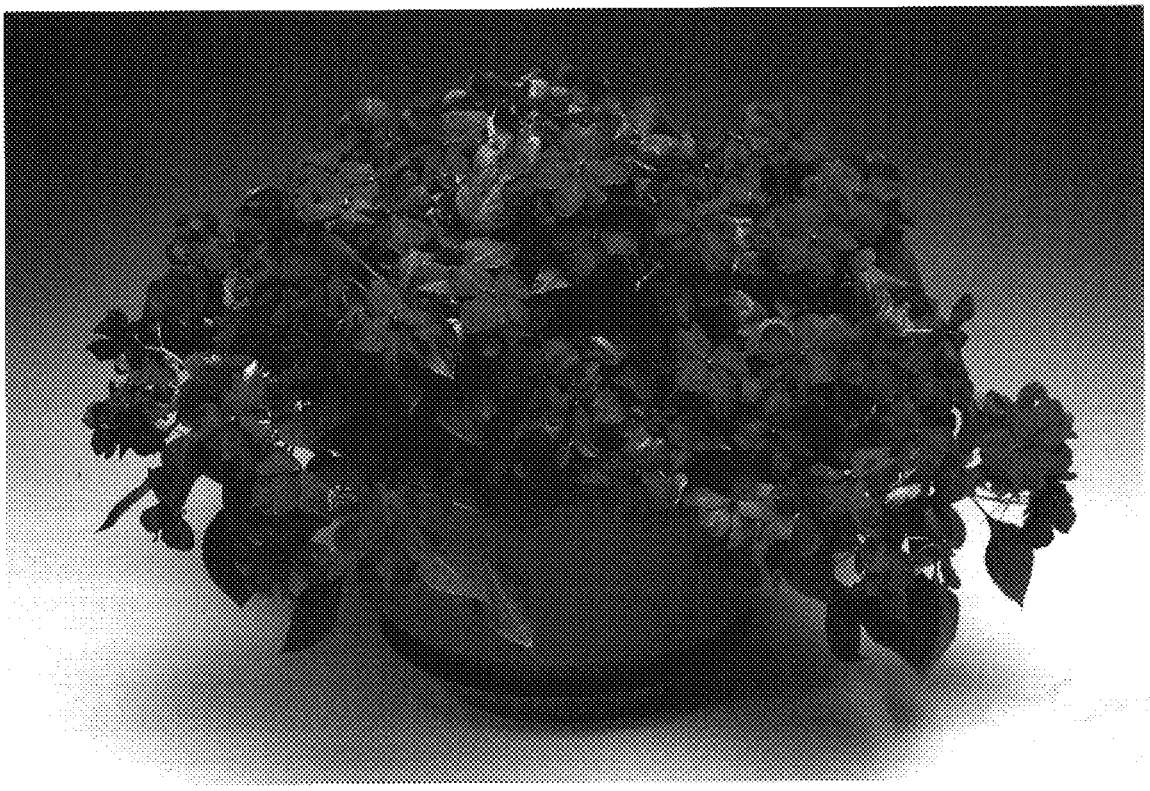

* * * * *